United States Patent
Sato

(10) Patent No.: US 9,737,221 B2
(45) Date of Patent: Aug. 22, 2017

(54) BIOLOGICAL INFORMATION MEASURING DEVICE

(71) Applicant: Seiko Epson Corporation, Tokyo (JP)

(72) Inventor: Reiko Sato, Azumino (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 14/833,374

(22) Filed: Aug. 24, 2015

(65) Prior Publication Data
US 2016/0058313 A1     Mar. 3, 2016

(30) Foreign Application Priority Data

Aug. 27, 2014 (JP) ................................. 2014-173295

(51) Int. Cl.
*A61B 5/00* (2006.01)
*A61B 5/024* (2006.01)

(52) U.S. Cl.
CPC .......... *A61B 5/02438* (2013.01); *A61B 5/681* (2013.01); *A61B 5/742* (2013.01); *A61B 5/746* (2013.01); *A61B 5/02427* (2013.01)

(58) Field of Classification Search
CPC ..... A61B 5/02438; A61B 5/681; A61B 5/742; A61B 5/746; A61B 5/02427
See application file for complete search history.

(56) References Cited

U.S. PATENT DOCUMENTS

2003/0176815 A1   9/2003   Baba et al.
2015/0209615 A1*  7/2015   Edwards ............ A61B 5/02438
                                                     482/9

FOREIGN PATENT DOCUMENTS

JP      2003-265441 A     9/2003

* cited by examiner

*Primary Examiner* — Scott Getzow
(74) *Attorney, Agent, or Firm* — Kilpatrick Townsend & Stockton LLP

(57) ABSTRACT

A biological information measuring device includes a display and a processor. The processor is adapted to generate heart rate information representing a heart rate of a living body, to specify a heart rate range of a plurality of predetermined heart rate ranges to which the heart rate belongs based on the heart rate information, and to control the display to display that the heart rate belongs to the specified heart rate range.

8 Claims, 14 Drawing Sheets

FIG. 12A NORMAL SETTING EXAMPLE

| HEART RATE ZONE 1 | 30~100 bpm |
|---|---|
| HEART RATE ZONE 2 | 101~130 bpm |
| HEART RATE ZONE 3 | 131~160 bpm |
| HEART RATE ZONE 4 | 161~190 bpm |
| HEART RATE ZONE 5 | 191~240 bpm |

FIG. 12B OVERLAP SETTING EXAMPLE

| HEART RATE ZONE 1 | 30~100 bpm |
|---|---|
| HEART RATE ZONE 2 | 101~130 bpm |
| HEART RATE ZONE 3 | 131~165 bpm |
| HEART RATE ZONE 4 | 160~190 bpm |
| HEART RATE ZONE 5 | 191~240 bpm |

BIOLOGICAL INFORMATION MEASURING DEVICE

This application claims priority to Japanese Patent Application No. 2014-173295, filed Aug. 27, 2014, the entirety of which is hereby incorporated by reference.

BACKGROUND

1. Technical Field

The disclosure relates to a biological information measuring device.

2. Related Art

In recent years, a wristwatch-type measuring device for measuring and displaying a heart rate of a user has been widely used. Such a measuring device includes, for example, a pulse sensor, and detects a pulse of the user by the pulse sensor. For example, JP-A-2003-265441 discloses a measuring device including a pulse sensor that is fixed to a finger of a user. Since the device can measure a heart rate based on the pulse, the user can check a change in heart rate by wearing the measuring device.

A measuring device of classifying a heart rate into a plurality of "heart rate zones (hereinafter, referred to as a zone)" and presenting to a user a zone to which a heart rate at a current point in time belongs has begun to appear. In such a measuring device, a predetermined value range is previously set to the heart rate for each zone.

Among recent wristwatch-type measuring devices, there is a device that presents a zone to a user by emitting colored light previously set for each zone. A presenting section that presents the zone to the user is a kind of display section (light emitting section).

Incidentally, among users, there are users who desire to set the value ranges of the heart rate corresponding to the respective zones such that the value ranges thereof overlap in the plurality of zones. For example, by setting the value ranges in this manner, it is easy to conduct a flexible running plan in which a heart rate corresponding to the upper half of the value range related to the zone where the heart rate is lower than the highest heart rate by one level is allowed in other sections while achieving the zone where the heart rate is the highest in a specific section of a running path.

However, in the configuration of the measuring device according to the related art, it is difficult to set the zones in this manner, and thus, the presenting section can present only the zones to which the value ranges are exclusively set.

Since a biological information measuring device is used by being worn on a body, there is a need for a biological information measuring device having improved usability by having a small size, a thin thickness and long-term durability of a power unlike the related art. Specifically, there is a need for a biological information measuring device capable of having a small size and a thin thickness by storing a pulse sensor within an external case and of ensuring durability of a power.

SUMMARY

An advantage of some aspects of the disclosure is that usability is improved by solving at least any one of portability (small size and thin thickness), visibility of a display and durability of a power.

A biological information measuring device according to one aspect of the disclosure includes a heart rate information generating section that generates heart rate information representing a heart rate of a living body; a specifying section that specifies a heart rate range of a plurality of predetermined heart rate ranges to which the heart rate belongs based on the heart rate information; display regions that respectively correspond to the plurality of heart rate ranges; and a controller that controls the display region corresponding to the heart rate range specified by the specifying section to display that the heart rate belongs to the specified heart rate range.

According to this aspect, two or more display regions are provided so as to respectively correspond to the plurality of heart rate ranges, and the respective heart rate ranges are respectively displayed on the corresponding display regions. Thus, when the value ranges of the heart rate corresponding to the respective heart rate ranges are set such that the plurality of heart rate ranges overlap each other, even though the measured heart rate belongs to the plurality of heart rate ranges, the respective display regions appropriately display that the heart rate belongs to the heart rate ranges.

The biological information measuring device according to another aspect of the disclosure is directed to the biological information measuring device according to the one aspect described above, which further includes an operation section that outputs an operation signal in response to an input operation of a user; and a setting section that sets a heart rate lower limit and a heart rate upper limit to each of the plurality of heart rate ranges based on the operation signal, in which the specifying section specifies a heart rate range of the plurality of heart rate ranges to which the heart rate belongs by referring to the heart rate lower limit and the heart rate upper limit set by the setting section.

According to this aspect, the user can respectively set the value ranges of the heart rate corresponding to the respective heart rate ranges to be desired values.

The biological information measuring device according to another aspect of the disclosure is directed to the biological information measuring device according to the one aspect described above, in which the plurality of heart rate ranges include a first heart rate range, and a second heart rate range, the display region corresponding to the first heart rate range is a first display region, and the display region corresponding to the second heart rate range is a second display region, the first heart rate range is a range from a first heart rate lower limit to a first heart rate upper limit, and the second heart rate range is a range which is from a second heart rate lower limit to a second heart rate upper limit and which is greater than the first heart rate lower limit and is less than the first heart rate upper limit, the specifying section specifies that the heart rate belongs to the first heart rate range and the second heart rate range when a heart rate represented by the heart rate information is greater than the second heart rate lower limit and is less than the first heart rate upper limit, and the controller controls the first display region to display that the heart rate belongs to the first heart rate range, and controls the second display region to display that the heart rate belongs to the second heart rate range.

According to this aspect, it is possible to set the value ranges of the heart rate corresponding to the heart rate ranges such that the plurality of heart rate ranges overlap with each other, and thus, it is easy to conduct a flexible running plan in which a heart rate corresponding to the upper half of the value range related to the heart rate range where the heart rate is lower than the highest heart rate by one level is allowed in other sections while achieving the heart rate range where the heart rate is the highest in a specific section of a running path. In the configuration of the biological information measuring device according to the related art, it is difficult to set the heart rate ranges in this manner. In addition, in the configuration of the biological information measuring device according to the related art, since it is difficult to individually express the plurality of heart rate ranges in this manner, the device can cope with only the heart rate ranges to which the value ranges are exclusively set.

The biological information measuring device according to another aspect of the disclosure is directed to the biological information measuring device according to the one aspect described above, in which the plurality of display regions are regions allocated to a display section that displays an image, and are arranged in a 12-o'clock direction of the display section.

According to this aspect, since the plurality of display regions are arranged on an upper side of the display section when the biological information measuring device is correctly positioned, the user can easily view the display regions.

The biological information measuring device according to another aspect of the disclosure is directed to the biological information measuring device according to the one aspect described above, which further includes an operation section that outputs an operation signal in response to an input operation of a user; an alarm section that alarms the user; and a setting section that sets an alarm heart rate range which is one heart rate range or a plurality of heart rate ranges which is an alarming target based on the operation signal, in which the controller controls the alarm section to give an alarm when a heart rate represented by the heart rate information belongs to the alarm heart rate range.

According to this aspect, the user can set the alarm heart rate range to be a desired value range, and thus, when the heart rate of the user belongs to the alarm heart rate range, the alarm section gives the alarm to the user. Thus, for example, by setting a dangerous heart rate that injures the user's health as the alarm heart rate range, even though the user does not constantly check their heart rate, since the user is alerted when the heart rate of the user reaches the dangerous heart rate, the user can focus on running.

The biological information measuring device according to another aspect of the disclosure is directed to the biological information measuring device according to the one aspect described above, which further includes an operation section that outputs an operation signal in response to an input operation of a user; an alarm section that alarms the user; and a setting section that sets a target heart rate range which is one heart rate range or a plurality of heart rate ranges which is excluded from an alarming target based on the operation signal, in which the controller controls the alarm section to give an alarm when a heart rate represented by the heart rate information does not belong to the target heart rate range.

According to this aspect, since the user can set the target heart rate range to be a desired value range, the user is alerted by the alarm section when the heart rate of the user is out of the target heart rate range. Thus, for example, by setting a target heart rate as the target heart rate range during running, since the user is alerted when their heart rate reaches the target heart rate even though the user does not constantly check their heart rate, the user can focus on running.

The biological information measuring device according to another aspect of the disclosure is directed to the biological information measuring device according to the one aspect described above, which further includes an operation section that outputs an operation signal in response to an input operation of a user; and a setting section that sets an alarm heart rate range which is one heart rate range or a plurality of heart rate ranges which is an alarming target based on the operation signal, in which the plurality of display regions is regions allocated to a display section that displays an image, and the controller displays an alarm in a region to which the display region is allocated when a heart rate represented by the heart rate information belongs to the alarm heart rate range.

According to this aspect, when the alarm is displayed on the display section, the display region regarding the heart rate range is not displayed on the display section. Thus, since it is possible to further increase an area in which the alarm is displayed, an alarming effect is improved.

BRIEF DESCRIPTION OF THE DRAWINGS

The disclosure will be described with reference to the accompanying drawings, wherein like numbers reference like elements.

FIGS. 12A and 12B are diagrams for describing a setting example of value ranges of the zones.

DESCRIPTION OF EXEMPLARY EMBODIMENTS

Figure 1:
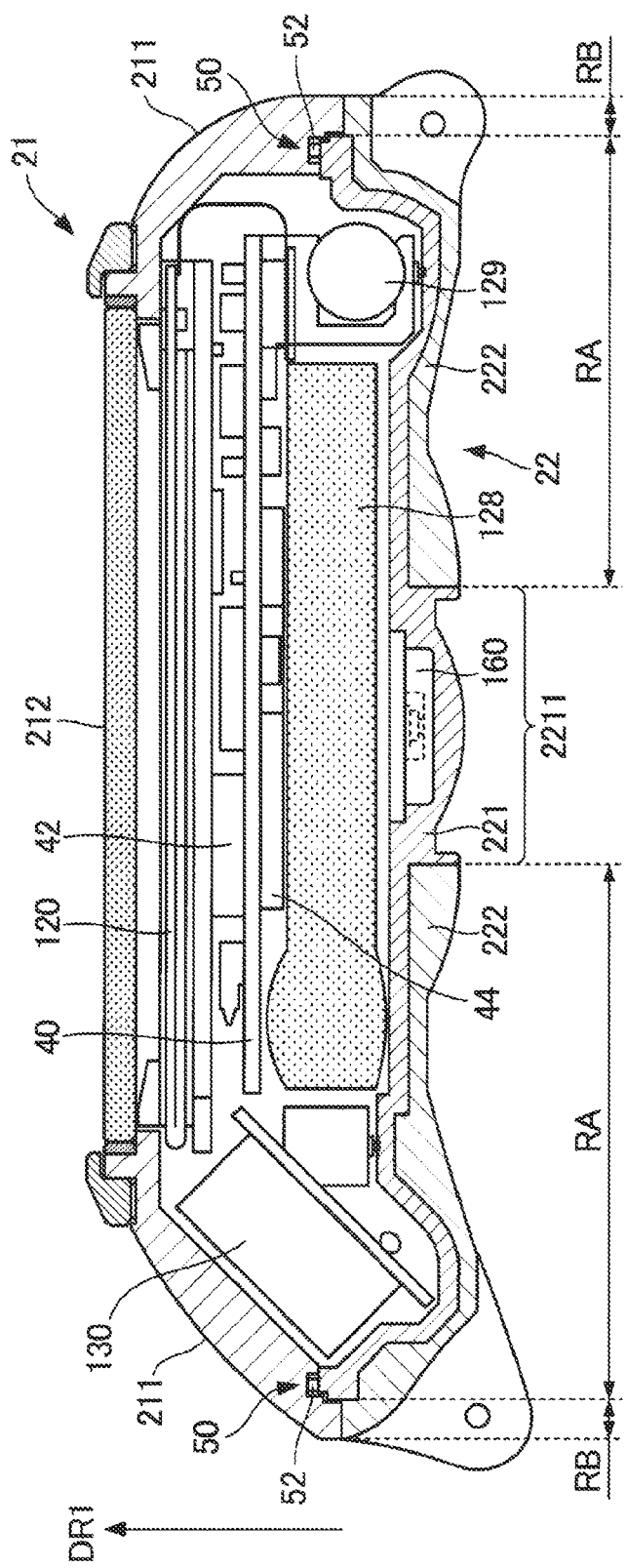
FIG. 1 is a sectional view of a biological information measuring device according to an exemplary embodiment of the disclosure.

Hereinafter, exemplary embodiments of the disclosure will be described. The present exemplary embodiments, to be described below, are not intended to inappropriately limit the content of the disclosure described in the appended claims. The entire configuration described in the present exemplary embodiment is not necessarily the essential configuration of the disclosure.

1. Method of Present Exemplary Embodiment

A method of the present exemplary embodiment will first be described. In a wearable-type biological information measuring device (so-called running watch) worn on the wrist of a user, a method of obtaining biological information by using a photoelectric sensor is known. For example, as a biosensor which is the photoelectric sensor, a pulse sensor may be considered, and it is possible to obtain a pulse signal such as a pulse rate by using the pulse sensor.

Hereinafter, an example in which a wristwatch-type device worn on the wrist is used will be described, but a biological information measuring device according to the present exemplary embodiment may be worn on the neck, the ankle, or other portions of the user. The biological sensor (photoelectric sensor) according to the present exemplary embodiment is not limited to the pulse sensor, and a photoelectric sensor of obtaining biological information other than the pulse signal may be used. The biological information measuring device according to the present exemplary embodiment may include a biological sensor other than the photoelectric sensor.

In the biological information measuring device including the photoelectric sensor, it is necessary to receive necessary light and to block unnecessary light. In the example in which the pulse sensor is used, since reflection light reflected from a test object (particularly, a portion including a blood vessel of a measuring target) includes a pulse component, it is necessary to receive the reflection light. However, since light other than the reflection light is a noise component, it is necessary to block the other light. Here, as the "other light", direct light which is emitted from a light emitter and is directly incident on a light receiver, reflection light reflected from another portion other than the test object, or ambient light such as sunlight or illumination light may be considered.

In order to appropriately control light to be transmitted and blocked, the biological information measuring device may include a light transmitter and a light blocker. For example, as will be described reference to FIG. 1, in a portion (a bottom case in the narrow sense) of the biological information measuring device which is provided close to the test object, the arrangement of the light transmitter and the light blocker may be considered.

When a use case of the biological information measuring device according to the present exemplary embodiment is assumed, a more appropriate device may be realized by satisfying various conditions in addition to the positional relationship between the light transmitter and the light blocker.

First, the biological information measuring device is required to have high waterproof performance. For example, since a circuit board 40, a battery (secondary battery 128), and a vibration motor (vibration section 129) are included in the inside (a space between a top case 21 and a bottom case 22 in the example of FIG. 1) of the biological information measuring device, low waterproof performance may pose a failure in these elements. Particularly, a wearable-type device such as a wristwatch type being worn during exercise and being used to present information such as exercise intensity may be considered. In this case, the skin surface of the user may become wet with sweat, and thus, inhibition of a risk of liquid or gas such as water vapor flowing in the device is required.

A panel frame 42 that guides a display panel such as a display section 120 is disposed on one surface of the circuit board 40, and a circuit case 44 that guides the secondary battery 128 is disposed on the other surface thereof.

An epoxy resin-based board containing a glass fiber is used as the circuit board 40, and wiring patterns made of a copper foil are formed on both surfaces of the circuit board. The panel frame 42 and the circuit case 44 are made of a resin such as polyacetal or polycarbonate.

Elements constituting a circuit that drives the photoelectric sensor to measure a pulse, a circuit that drives the display section 120, and a circuit that controls the respective circuits are mounted on the circuit board 40. A connection electrode with the display section 120 is formed on one surface of the circuit board 40, and is electrically conducted to an electrode of the display section 120 through a non-illustrated connector.

On the display section 120, pulse measurement data such as a pulse rate or time information such as a current time is displayed depending on the respective modes. The respective modes will be described below.

A rechargeable button-type secondary battery 128 (lithium secondary battery) is stored in the circuit case 44. The secondary battery 128 supplies a power to a circuit of which both pole terminals are connected to the circuit board 40 to control the power. The power is converted into a predetermined voltage in this circuit, and is then supplied to the respective circuits. Thus, the supplied power operates the circuit that drives the photoelectric sensor to detect the pulse, the circuit that drives the display section 120, and the circuit that controls the respective circuits. The secondary battery 128 is charged through a pair of charging terminals that is electrically conducted to the circuit board 40 by a conduction member such as a coil spring. Here, although it has been described that the secondary battery 128 is used as the battery, a primary battery unnecessary to charge may be used as the battery.

As a mode of use of the biological information measuring device 1 according to the present exemplary embodiment, it is assumed that the measurement of an exercise state and the measurement of health are included. Thus, the present applicant realizes the biological information measuring device 1 capable of being continuously used for a long period of time by taking into account the control method and the configuration of a pulse sensor 160, the circuit board 40, or other components. For example, a secondary battery having a capacity of 150 mAh may be used as a secondary battery 60, to be described below.

Second, the case (the top case and the bottom case) is required to have high strength. As stated above, various components are arranged within the device, but various forces are applied to the wearable-type biological information measuring device in cooperation with the motion of the user. For example, when the user is jogging, a pressing force or a twisting force is applied to the device due to motion such as the swinging of their arm. In this case, when such a force is applied to the internal component such as the circuit board 40, a failure occurs in this component.

Third, the device is required to allow the user to feel comfortable while wearing the device. The wearable-type biological information measuring device needs to be worn on the user during the use of the device. If the device is used during exercise as stated above, it is necessary to continuously wear the device for a period of time (for example, from the start of exercise to the end thereof) necessary to obtain data. Alternatively, in an example in which the health of the user is determined, it is necessary to continuously obtain the biological information for a long period of time (for example, 12 hours, 24 hours, or a span of several days), and the device is worn in this period of time. For this reason, it is not preferable that the exercise or daily life of the user is inhibited due to the wearing of the biological information measuring device, and a feeling of comport while wearing the device becomes an important element. Specifically, the biological information measuring device may be a small type (thin type), and may be lightweight. That is, it is preferable that the biological information measuring device receives necessary light and blocks unnecessary light, has high waterproof performance and high strength, is a small type, and is lightweight.

Although it is illustrated in FIG. 1 that the case 20 includes the top case 21 and the bottom case 22, and the bottom case 22 includes a light transmitter 221 and a light blocker 222, the present exemplary embodiment is not limited thereto. For example, the case 20 may be formed using an integral member. Alternatively, various modification examples in which a ceiling plate which is a transparent plate-like member and the case 20 which is combined with the ceiling plate and is made of a resin material are used are possible. Hereinafter, although it will be described in the present specification that the case 20 having a structure shown in FIG. 1, the method of the present exemplary embodiment is applicable to a case where the case 20 having another structure in which the light transmitter 221 and the light blocker 222 are provided is used. In FIG. 1, the configuration of the pulse sensor 160, a detection window 2211, and peripheral portions of the detection window 2211 is simplified.

In such a configuration, it is possible to use appropriate light during measurement in the photoelectric sensor by using the light transmitter 221 and the light blocker 222. In this case, it is easy to manufacture the case 20 (particularly, the bottom case 22) as long as the light transmitter 221 and the light blocker 222 are integrally formed.

In order to meet the aforementioned first and second requirements, the case 20 that is not easily deformed may be used. When the case 20 is easily deformed, a path in which a liquid or water vapor flows may be formed due to the deformation, or a pressure from the outside may be easily transferred to the internal components. As the flow path herein, a gap between the light transmitter 221 and the light blocker 222 may be considered. For example, even though the light transmitter 221 and the light blocker 222 are formed through dual-injection molding by using a common resin base, since the surfaces thereof are merely stuck together by being slightly melt, there is a possibility that the water vapor will enter a small gap formed therebetween. However, it is possible to suppress this phenomenon by using the case 20 that is not easily deformed. In general, the case can have a structure that is not easily deformed by increasing the thickness of the member. However, the biological information measuring device is not able to have a small size and be lightweight in such a manner, and thus, it is difficult to meet the aforementioned third requirement.

In this regard, in the present embodiment, by forming the light blocker 222 by using a glass-containing resin material, the light blocker 222 is not easily deformed. For this reason, it is not necessary to thicken the thickness of the light blocker 222, and thus, it is possible to allow the biological information measuring device 1 to have a thin thickness and be lightweight while achieving high waterproof performance and high strength. That is, by forming the light blocker 222 by using the glass-containing resin material, it is possible to efficiently solve the aforementioned various problems.

By allowing the biological information measuring device 1 to have a thin thickness and be lightweight, it is possible to expect an effect of increasing detection precision of the biological information (an effect of suppressing a decrease in precision). If the biological information measuring device 1 is thick, when the user wears a long-sleeved cloth, a sleeve touches the device, and thus, the device may swing due to the motion of the sleeve. The user wants to use the biological sensor such as the pulse sensor while bringing the sensor into close contact with their skin. However, since the device may not maintain the contract due to the swinging, measurement precision may be degraded. In this regard, when the biological information measuring device 1 is allowed to have a thin thickness, it is possible to suppress the non-contact of the device caused by touching the sleeve, and it is possible to increase the detection precision.

Hereinafter, a specific configuration example of the biological information measuring device 1 according to the embodiment will be described.

2. Configuration of Biological Information Measuring Device

Figure 2A:
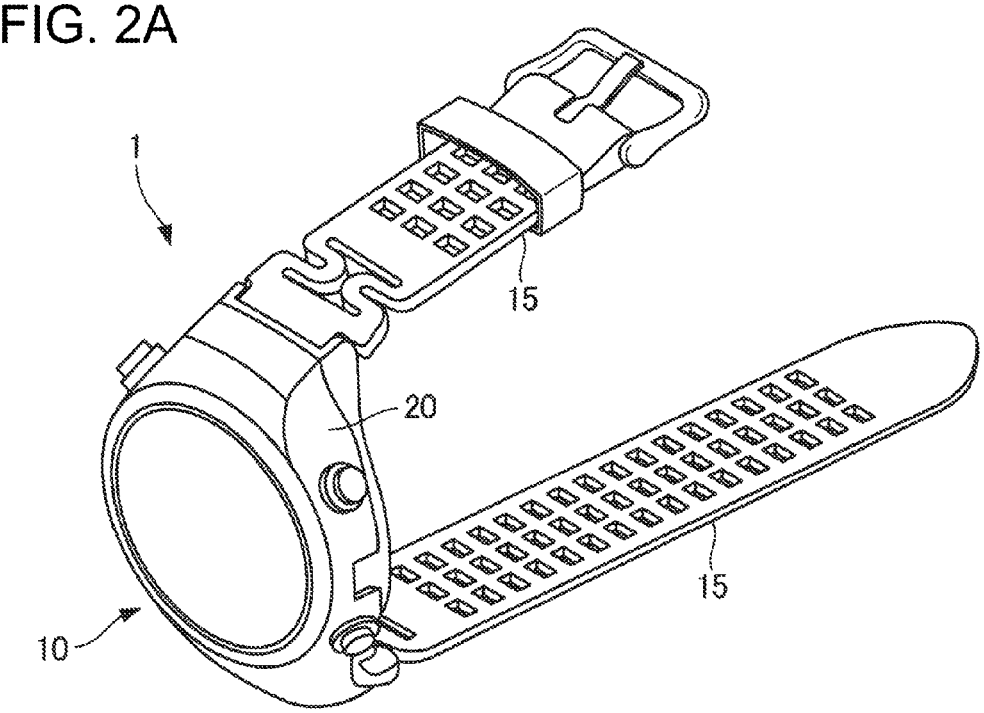
FIGS. 2A and 2B are perspective views showing the biological information measuring device according to the exemplary embodiment of the disclosure.
Figure 2B:
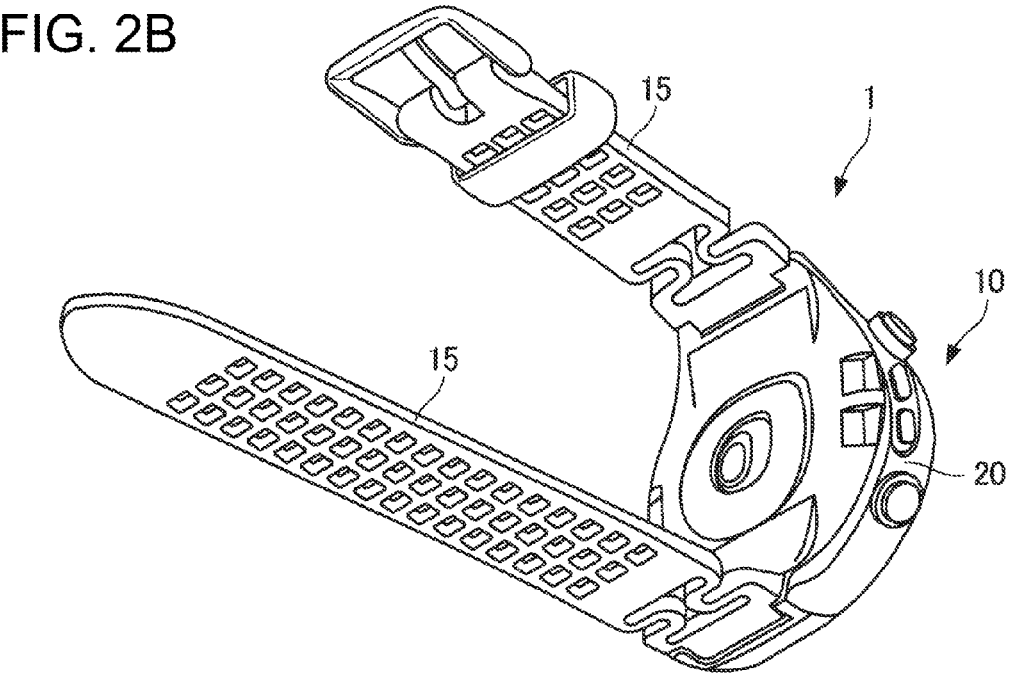

FIGS. 2A and 2B are perspective views of the biological information measuring device 1 according to the present exemplary embodiment. FIG. 2A is a perspective view when viewed from the top case 21, and FIG. 2B is a perspective view when viewed from the bottom case 22. The biological information measuring device 1 according to the present exemplary embodiment is worn on a given portion (for example, the wrist) of the user to detect the biological information such as the pulse signal. The biological information measuring device 1 includes a device main body 10 that comes in close contact with the user to detect the biological information, and a band 15 that is attached to the device main body 10 to allow the device main body 10 to be worn on the user.

Figure 3B:
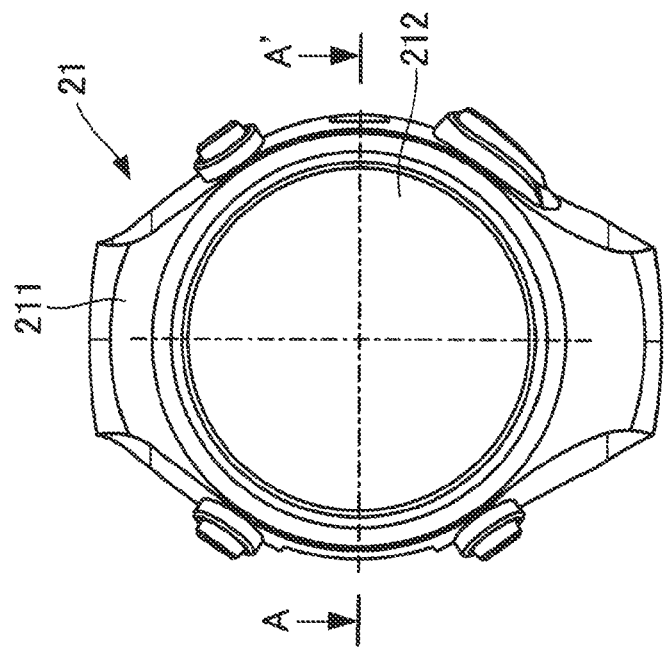
FIGS. 3A and 3B are plan views showing the biological information measuring device according to the exemplary embodiment of the disclosure.
Figure 3A:
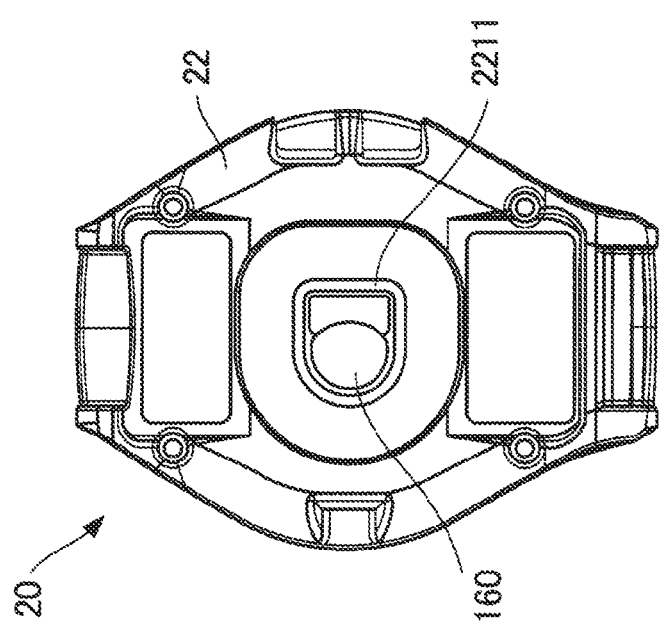

The device main body 10 includes the top case 21, and the bottom case 22. FIGS. 3A and 3B are diagrams showing the portion of the device main body 10 of the biological information measuring device 1. FIG. 3A is a plan view of the device main body in a direction from the bottom case 22 to the top case 21, that is, a direction in which the device main body is observed from the test object (user's wrist) in a state where the biological information measuring device 1 is used by being worn on the user. FIG. 3B is a plan view of the device main body opposite to FIG. 3A, that is, in a direction from the top case 21 to the bottom case 22. That is, FIG. 3A is a plan view that primarily shows the structure of the bottom case 22, and FIG. 3B is a plan view that primarily shows the structure of the top case 21.

As shown in FIG. 3A, the detection window 2211 is provided in the bottom case 22, and the pulse sensor 160 is provided in a position corresponding to the detection window 2211. The detection window 2211 is configured to transmit light. Light emitted from a light emitter of the photoelectric sensor (a sensor that detects a pulse) provided in the pulse sensor 160 is transmitted through the detection window 2211, and is applied to the test object. Reflection light reflected from the test object is also transmitted through the detection window 2211, and is received by a light receiver of the pulse sensor. That is, by providing the detection window 2211, it is possible to detect the biological information by using the photoelectric sensor. Specifically, the detection window 2211 may be realized by the light transmitter 221 (see FIG. 1) (the light transmitter 221 includes the detection window 2211). A specific structure of the light transmitter 221 will be described below.

As shown in FIG. 3B, the top case 21 may include a body 211, and a glass plate 212. In this case, the body 211 and the glass plate 212 may be used as outer walls for protecting an internal structure, and may be configured such that the user can view a display on a liquid crystal display (the display section 120 shown in FIG. 1) that is provided directly under the glass plate 212 through the glass plate 212. That is, in the biological information measuring device 1 according to the present exemplary embodiment, various information items such as the detected biological information, information indicating an exercise state, and time information are displayed on the display section 120, and the display may be presented to the user from the top case 21. It has been described in the present exemplary embodiment that the ceiling plate of the biological information measuring device 1 is implemented by the glass plate 212. However, the ceiling plate may be made of a material such as transparent plastic other than glass as long as the display section 120 is a viewable transparent member, and a member having strength capable of protecting the configuration included within the case 20 of the display section 120.

Next, an example of a detailed sectional structure of the device main body 10 (see FIGS. 2A and 2B) of the biological information measuring device 1 will be described with reference to FIG. 1. FIG. 1 is a sectional view taken along A-A' in FIG. 3B, and an upper side on paper of FIG. 1 is the top case 21, and a lower side on paper is the bottom case 22.

As shown in FIG. 1, the device main body 10 includes the pulse sensor 160, the circuit board 40, the panel frame 42, the circuit case 44, the secondary battery 128, the display section 120, the vibration section 129, and an antenna 130 in addition to the top case 21 and the bottom case 22. The configuration of the biological information measuring device 1 is not limited to FIG. 1, and the other configuration may be added, or a part of the configuration may be omitted.

The pulse sensor 160 includes the photoelectric sensor as described above. In such a configuration, since the pulse sensor 160 includes the photoelectric sensor, the biological information measuring device 1 can measure, for example, a pulse as the biological information due to characteristics thereof, and can derive a pulse rate, the hardness of a blood vessel, a state regarding the exercise, or a psychological state based on this measured information.

In the photoelectric sensor, light, which is applied to the wrist of the user from a light emitter such as a light emitting diode (LED) and is reflected from a blood vessel of the wrist, is concentrated by a condensing mirror, and the concentrated light is received by a light receiver such as a photo diode. In this case, the photoelectric sensor measures a pulse of the user by using a phenomenon in which there is a difference in reflectivity of light at the time of expansion and contraction of the blood vessel. For this reason, it is preferable that the pulse sensor 160 is pressed against the wrist such that light as measurement noise is not received by a photodetector of the photoelectric sensor. It is more preferable that the pulse sensor comes in close contact with the wrist.

The panel frame 42 that guides the display panel such as the display section 120 is disposed on one surface of the circuit board 40, and the circuit case 44 that guides the secondary battery 128 is disposed on the other surface thereof.

An epoxy resin-based board containing glass fiber is used as the circuit board 40, and wiring patterns made of a copper foil are formed on both surfaces. The panel frame 42 and the circuit case 44 are made of a resin such as polyacetal or polycarbonate.

A memory controller (MCU) 136 which controls a display on the display section 120 or processes a satellite signal received by the antenna 30 and includes various ICs is mounted on the circuit board 40. The MCU 136 is an example of a processor. Running information such as a running speed, a running distance, a running time, a running pace (for example, a necessary time (minute) per 1 km), a pitch (the number of steps per 1 minute), and the number of steps is displayed on the display section 120 under the control of a main controller mounted on the MCU 136. A connection electrode with the display section 120 is formed on one surface of the circuit board 40, and is electrically conducted to an electrode of the display section 120 through a non-illustrated connector.

As stated above, the biological information measuring device 1 according to the present exemplary embodiment includes the secondary battery 128 provided at the case 20, and the circuit board 40 that is provide on a side of the case 20 opposite to a contact surface with the test object with respect to the secondary battery 128 and on which a processing unit of the biological information measuring device 1 is mounted. In other words, when the biological information measuring device 1 has the configuration of FIG. 1, the biological information measuring device 1 includes the secondary battery 128 provided between the top case 21 and the bottom case 22, and the circuit board 40 that is provided between the secondary battery 128 and the top case 21 and on which the processing unit of the biological information measuring device 1 is mounted. Here, the secondary battery 128 and the circuit board 40 may be provided at the center of the biological information measuring device 1 in a plan view (corresponding to FIG. 3A) viewed from the contact surface with the test object.

In a plan view when the case 20 (the bottom case 22 in the narrow sense) is viewed from the contact surface with the test object, the biological information measuring device 1 may include the vibration section 129 (the vibrating motor) provided closer to an end of the biological information measuring device 1 than the secondary battery 128. For example, the vibration section 129 may transmit any notification to the user, and may be used as a user interface different from the display section 120. In the example of FIG. 1, the vibration section 129 may be provided closer to a right end than the secondary battery 128.

Next, the sectional structure of the light transmitter 221 and the light blocker 222 will be described in detail. As can be seen from FIG. 1, the light blocker 222 is provided in a portion other than the detection window 2211 so as to surround the light transmitter 221 from the test object.

In the detection window 2211, the light transmitter 221 is not surrounded by the light blocker 222. In other words, the detection window 2211 is realized by the light transmitter 221. Thus, as described above, in the photoelectric sensor provided in the pulse sensor 160, it is possible to irradiate the test object with light from a light emitter 311 and to receive reflection light from the test object by the light receiver, and thus, it is possible to detect the biological information such as the pulse signal.

Meanwhile, in the portion other than the detection window 2211, the light transmitter 221 is surrounded by the light blocker 222 from the test object (the lower side on the paper of FIG. 1). In so doing, it is possible to limit light incident on the pulse sensor 160. Thus, it is possible to inhibit light as a noise source, for example, ambient light such as sunlight or illumination light from being received while receiving light desired to receive, that is, reflection light which is applied from the light emitter and is reflected from the test object. Accordingly, it is possible to improve detection precision of the biological information.

The structure in which the light blocker 222 surrounds the light transmitter 221 may be grasped from a different viewpoint. Specifically, in the biological information measuring device 1 according to the present exemplary embodiment, while the biological information measuring device 1 is worn on the user (test object), when a direction (a direction from the bottom case 22 to the top case 21 in the narrow sense) from the test object to the case 20 is represented as a first direction DR1, the light transmitter 221 is provided in the portion other than the detection window 2211 in the first direction DR1 of the light blocker 222.

Since the light transmitter 221 transmits light, a portion where the light transmitter 221 is provided needs to be determined by taking into account a possibility that light will flow through this portion. Here, since the light transmitter 221 is provided at the bottom case 22, a light incident direction to be considered is a direction from the test object to the bottom case 22, that is, the first direction DR1. In this case, if the light transmitter 221 is provided close to the DR1 of the light blocker 222, since it is considered that light incident on the light transmitter 221 other than the detection window 2211 is influenced by the blocking of the light blocker 222, it is possible to inhibit light as a noise source from being incident on the pulse sensor 160.

As can be seen from the example of FIG. 1, providing the light transmitter 221 in the DR1 of the light blocker 222 does not mean that the light transmitter 221 is provided in the DR1 across the entire region of the light blocker 222. For example, in a region indicated by RB of FIG. 1, a region where the light transmitter 221 is not disposed may be present in the DR1 of the light blocker 222. That is, providing the light transmitter 221 in the DR1 of the light blocker 222 may mean that the light blocker 222 is provided in a direction opposite to the DR1 except for the portion of the detection window 2211 when the light transmitter 221 is provided. Specifically, in a region indicated by RA of FIG. 1, that is, a region other than the detection window 2211 where the light transmitter 221 is provided, the light transmitter 221 is provided close to the DR1 than the light blocker 222.

Here, the light transmitter 221 is made of a resin material, and the light blocker 222 is made of a glass-containing resin material in which glass (a glass fiber in the narrow sense) is contained. Specifically, the light transmitter 221 may be made of polycarbonate, an ABS resin or an acrylic resin, and the light blocker 222 may be made of polycarbonate in which glass is contained, an ABS resin in which glass is contained, or an acrylic resin in which glass is contained.

That is, the light blocker 222 according to the present exemplary embodiment may be made of fiber reinforced plastics (FRP), or may be made of glass fiber reinforced plastics (GFRP) using glass fiber as fiber used for reinforcement. In the GFRP, a thermoplastic resin may be used as a resin used together with a glass fiber, and in the present exemplary embodiment, polycarbonate or an ABS resin may be used as the thermoplastic resin. Although a thermoplastic acrylic resin and a thermosetting acrylic resin are known as the acrylic resin, any of them may be used in the present exemplary embodiment. Since the GFRP is low cost among the FRPs and is general plastics, it is possible to easily realize the light blocker 222 according to the present exemplary embodiment by adopting the GFRP. As the resin material in the GFRP, various resin materials such as a polyester resin, a vinylester resin, an epoxy resin and a phenol resin may be used, and the light blocker 222 according to the present exemplary embodiment may be made by widely using these materials.

By adopting the structure described above, it is possible to allow the device to have a small size (a thin thickness) and lightweight. Specifically, it is possible to reduce the weight of the biological information measuring device 1 according to the present exemplary embodiment to be 60 g. As a result, it is possible to allow a plane size of an external case (case 20) to be 6 cm or less or a case thickness to be 15 mm or less. Here, as shown in FIG. 3A to be described below, the plane size of the case 20 represents a size in a plan view viewed in a direction in which the test object (the user's wrist) is observed when the biological information measuring device 1 is used by being worn on the user, and the case thickness represents a size in a direction (for example, the direction DR1 in FIG. 1) perpendicular to the case. Specifically, it is possible to set the maximum length of the case 20 in the plan view to be 6 cm or less and the maximum thickness in the direction DR1 to be 15 mm or less.

Figure 4:
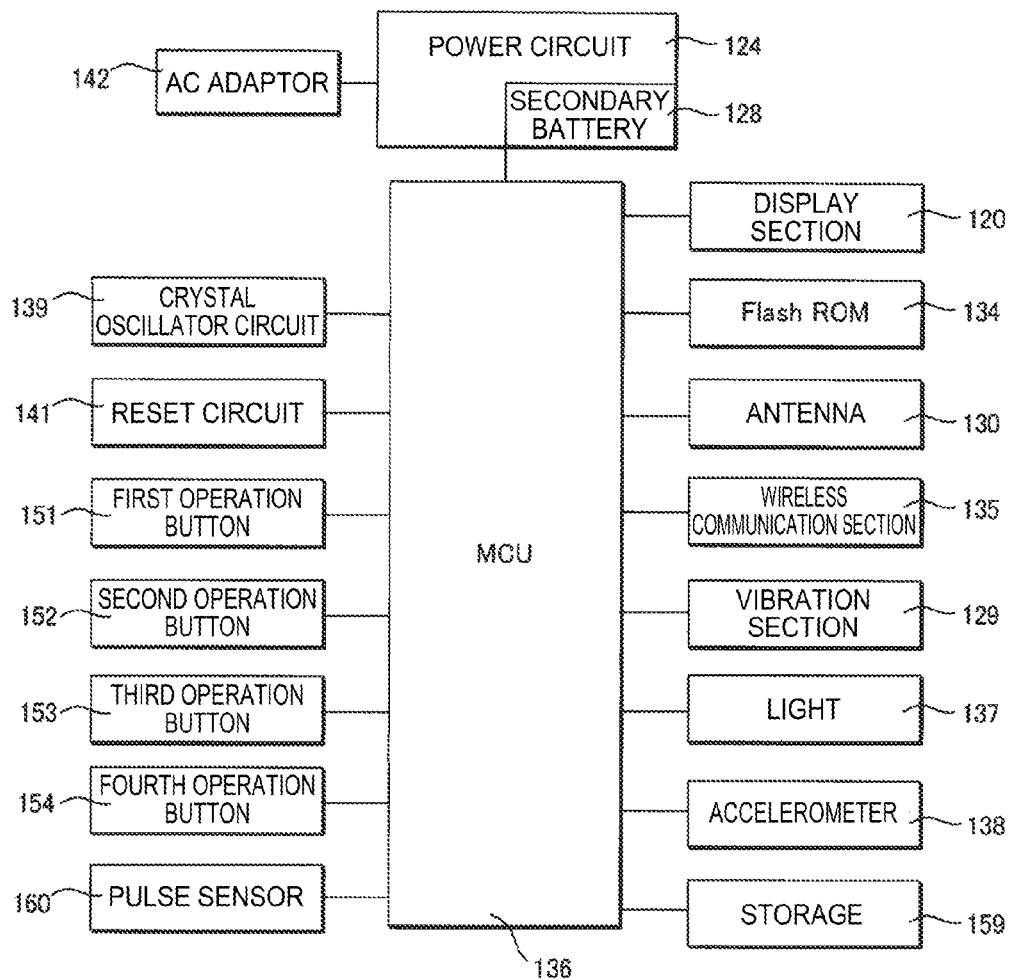
FIG. 4 is a diagram showing a system configuration of the biological information measuring device according to the exemplary embodiment of the disclosure.

FIG. 4 is a block diagram showing an example of a system configuration of the biological information measuring device 1. As shown in this drawing, a power circuit 124, the display section 120, a flash ROM 134, the antenna 130, a wireless communication section 135, the vibration section 129, a light 137, an accelerometer 138, a crystal oscillator circuit 139, a reset circuit 141, a storage 159, the pulse sensor 160, and operation buttons 151 to 154 are connected to the MCU 136 in the biological information measuring device 1.

The MCU 136 includes a memory that stores programs therein, and performs a generating process of time information, a tap detecting process, to be described below, a storing process of a user running state, and a speed calculating process in addition to controlling the respective components of the biological information measuring device 1. When the power circuit 124 is connected to an AC adaptor 142 through a connection terminal (not shown), the power circuit charges the secondary battery 128. The secondary battery 128 supplies a drive power to the display section 120 or the antenna 130.

For example, time difference information is stored in the flash ROM 134. The time difference information is information in which time difference data (correction amount to UTC correlated with a coordinate value (for example, latitude and longitude)) is defined. As will be described below, the correlation between a body vibration frequency and a speed is also stored in the flash ROM 134.

The antenna 130 performs a process of obtaining satellite information such as satellite orbit information, GPS time information, or positional information included in a navigation message from a satellite signal having a bandwidth of, for example, 1.5 GHz.

The wireless communication section 135 performs wireless communication between the biological information measuring device 1 and a personal computer, and transmits log data stored in the biological information measuring device 1 to the personal computer. The light 137 irradiates the display section 120 with light through an operation of the user using the operation buttons, and allows the user to easily view the device even at night. Although not shown, a buzzer used to notify the user of the completion of a setting process is also provided.

The crystal oscillator circuit 139 is a crystal oscillator circuit provided with a temperature compensation circuit, and generates a reference clock signal having a substantially constant frequency irrespective of a temperature. The reset circuit 141 is used to reset a measurement state of the biological information measuring device 1 in response to a predetermined operation performed by the user.

Here, operation modes of the biological information measuring device 1 according to the present exemplary embodiment, and primary functions of the operation buttons 151 to 154 related to switching between the operation modes will be described in detail.

The biological information measuring device 1 according to the present exemplary embodiment includes at least three operation modes of a "time display mode" which is a first mode, a "measurement mode" which is a second mode, and a "heart rate display mode" which is a third mode.

Figure 5:
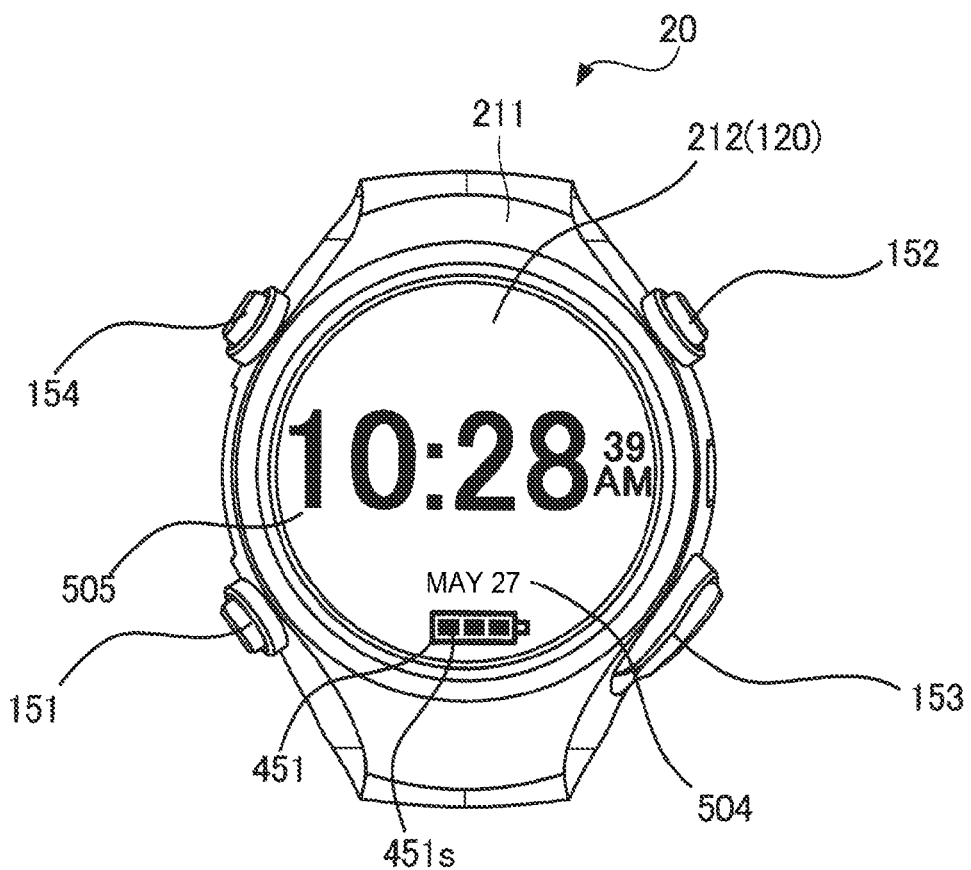
FIG. 5 is a diagram showing a display example of a display section when the biological information measuring device is in a "time display mode".

FIG. 5 is a diagram showing a display example of the display section 120 when the biological information measuring device 1 is in the "time display mode". The time display mode refers to an operation mode that is set when the biological information measuring device 1 is primarily used for a time display (as a wristwatch).

In the time display mode, the pulse sensor 160 (photoelectric sensor) and the antenna 130 are set in a stop state by the MCU 136, and do not perform a process of obtaining a pulse signal and a process of obtaining satellite information. As a primary display, time information 505 is displayed on the display section 120 as shown in FIG. 5. In the example shown in FIG. 5, date and time information 504 is also displayed on the display section 120.

A battery indicator 451 shown in FIG. 5 is an indicator that indicates a remaining amount of the secondary battery 128, and represents that the smaller the number of indicated rectangular marks 451s is, the smaller the remaining amount of the secondary battery 128 is.

Figure 6:
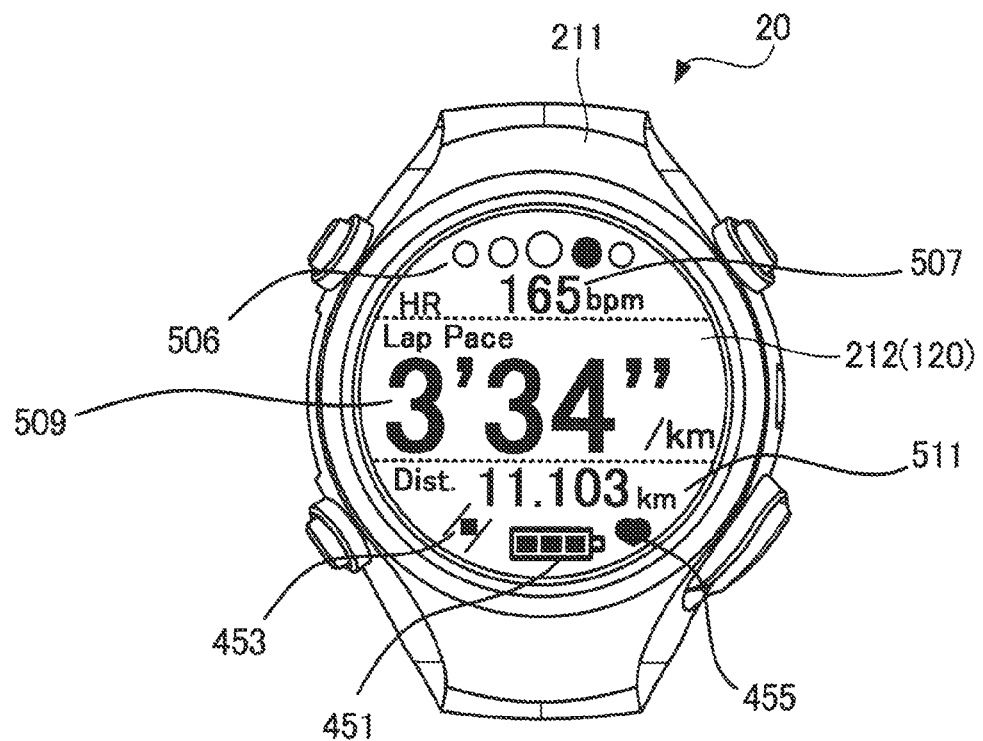
FIG. 6 is a diagram showing a display example of the display section when the biological information measuring device is in a "measurement mode".

FIG. 6 is a diagram showing a display example of the display section 120 when the biological information measuring device 1 is in the "measurement mode". The measurement mode refers to an operation mode that is set when the biological information measuring device 1 is used as a so-called running watch.

In the measurement mode, the pulse sensor 160 and the antenna 130 are set in an operation state by the MCU 136, and perform a process of obtaining the pulse signal and a process of obtaining the satellite information. A satellite indicator 453 shown in this drawing is an indicator indicating that the antenna 130 is an operation state. A heart indicator 455 shown in this drawing is an indicator indicating that the pulse sensor 160 is in an operation state.

A zone indicator 506 is an indicator indicating any one of a plurality (five in this example) of predetermined heart rate zones (value ranges of the heart rate defined by an upper limit and a lower limit; heart rate ranges) to which a current heart rate of the user belongs.

Here, five circle marks constituting the zone indicator 506 correspond to "Heart Zone 1", "Heart Zone 2", "Heart Zone 3", "Heart Zone 4", and "Heart Zone 5" in sequence from the left, and the circle mark turned on (a black mark in this drawing) is the heart zone to which the current heart rate of the user belongs. In the example of FIG. 6, the heart rate of the user belongs to Heart Zone 4. Hereinafter, the heart zone is simply referred to as a "zone".

In the measurement mode, the MCU 136 calculates the number of times (hereinafter, referred to as a "heart rate") the heart beats for a predetermined period of time (1 minute in this example) based on the pulse signal obtained by the pulse sensor 160, generates heart rate information representing the heart rate, stores the generated information in the storage 159, and displays heart rate information 507 on the display section 120 as shown in FIG. 6.

The heart rate may be an actual measurement value, or may be an estimation value. A time interval of calculating and storing the heart rate information and an update interval of the heart rate information 507 displayed on the display section 120 are arbitrarily set. "HR" shown in FIG. 6 is an abbreviation of the heart rate, and "bpm" is an abbreviation of "beat per minute".

In the measurement mode, the MCU 136 calculates lap pace information representing a time (hereinafter, referred to as a "lap pace") necessary for the user to run 1 km based on, for example, the satellite information and the time information, and displays lap pace information 509 on the display section 120 as shown in FIG. 6. The example shown in this drawing shows that the lap pace is 3 minutes 34 seconds [/km].

For example, in the measurement mode, the MCU 136 calculates cumulative movement distance information representing a cumulative movement distance based on the satellite information, and displays cumulative movement distance information 511 on the display section 120 as shown in FIG. 6. The example in this drawing shows that the cumulative movement distance is 11.103 km. In FIG. 6, "Dist." is an abbreviation of a distance.

Figure 7A:
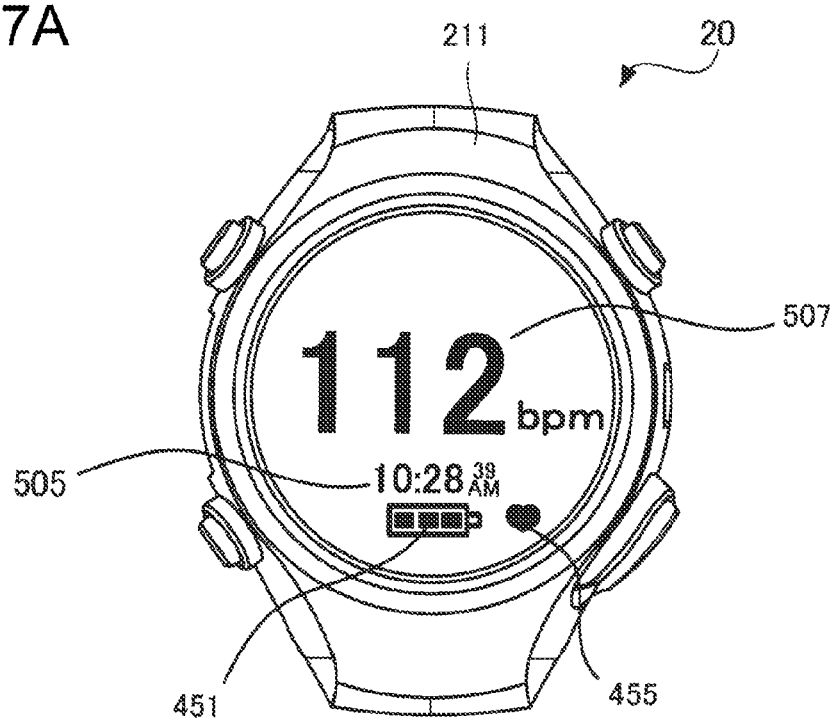
FIGS. 7A and 7B are diagrams showing a display example of the display section when the biological information measuring device is in a "heart rate display mode" and a display example of a "preparation screen".

FIG. 7A is a diagram showing a display example of the display section 120 when the biological information measuring device 1 is in the "heart rate display mode". The heart rate display mode is an operation mode that is set when the user wants to temporarily know a heart rate at any point in time.

A primary difference between the heart rate display mode and the measurement mode is that the antenna 130 is set in a stop state in the heart rate display mode and the heart rate information is not stored in the storage 159. Thus, in the heart rate display mode, power consumption and process load required for a process of obtaining the satellite information and calculating various information items by setting the antenna 130 in an operation state are reduced, and a storage capacity of the storage 159 is prevented from being wasted.

In the heart rate display mode, since the pulse sensor 160 is set in an operation state, the heart indicator 455 is displayed on the display section 120 in the measurement mode, as shown in FIG. 7A.

In the heart rate display mode, the MCU 136 calculates the heart rate based on the pulse signal obtained by the pulse sensor 160, and displays the heart rate information 507 representing the heart rate, as a primary display, on the display section 120, as shown in FIG. 7A.

The heart rate may be an estimation value as in the measurement mode, or may be an actual measurement value. As shown in FIG. 7A, the time display 505 together with the heart rate information 507 may be displayed on the display section 120.

As will be described in detail below, in order for the biological information measuring device 1 to actually calculate the heart rate information from the pulse signal and to display the calculated information while changing the operation mode from the time display mode to the heart rate display mode by a predetermined operation, a predetermined preparation period of time after the pulse sensor 160 is set in an operation state is required. A process performed by the MCU 136 for this preparation period of time will be described with reference to FIG. 9.

Figure 7B:
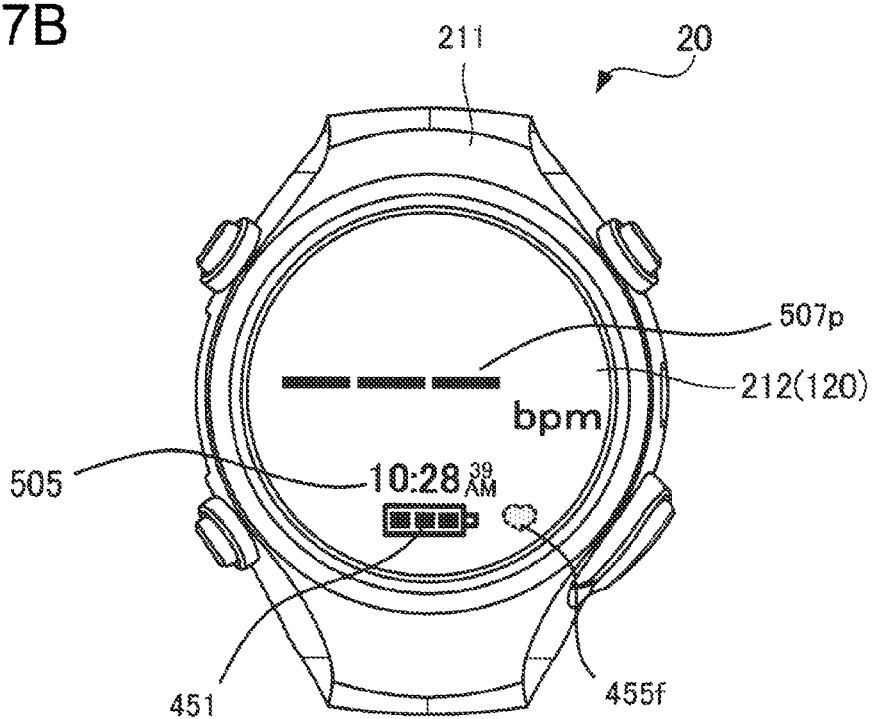

For example, a "preparation screen" shown in FIG. 7B is displayed on the display section 120 for this preparation period of time. Heart rate preparation information 507p such as "---" is displayed in a position where the heart rate information 507 is displayed in the heart rate display mode on the preparation screen. A flickering heart indicator 455f is displayed in the position where the heart indicator 455 is displayed in the heart rate display mode.

Incidentally, the biological information measuring device 1 is normally set in the time display mode shown in FIG. 5, and changes the operation mode to another mode, to be described below, in response to an operation of the operation buttons 151 to 154. Hereinafter, a function regarding the change of the operation mode among the functions of the operation buttons 151 to 154 will be primarily described.

For example, as shown in FIG. 5, the operation buttons 151 to 154 that are manually operated by the user are provided to protrude outward from the side surface of the case 20. Specifically, a first operation button (hereinafter, referred to as a "first button") 151 and a fourth operation button (hereinafter, referred to as a "fourth button") 154 are arranged within a range which is from a 6-o'clock position to a 12-o'clock position and includes a 9-o'clock position, and a second operation button (hereinafter, referred to as a "second button") 152 and a third operation button (hereinafter, referred to as a "third button") 153 are arranged within a range which is from a 12-o'clock position to a 6-o'clock position and includes a 3-o'clock position.

One of the functions of the first button 151 is a function of changing the operation mode from the "time display mode" to the "heart rate display mode". Specifically, when the biological information measuring device 1 is in the time display mode, if an operation signal representing that the first button 151 is pressed through a short pressing operation (hereinafter, simply referred to "short pressing") is output from the first button 151, the MCU 136 performs a process of changing the operation mode of the biological information measuring device 1 to the heart rate display mode.

One of the functions of the second button 152 is a function of changing the operation mode from the "time display mode" to the "measurement mode". Specifically, when the biological information measuring device 1 is in the time display mode, if an operation signal representing that the second button 152 is pressed through a long pressing operation (hereinafter, simply referred to as "long pressing") is output from the second button 152, the MCU 136 performs a process of changing the operation mode of the biological information measuring device 1 to the measurement mode. The changing of the operation mode to the measurement mode may be performed such that the second button 152 is pressed not through the long pressing but through the short pressing.

One of the functions of the third button 153 is a function of resetting the measurement state in the measurement mode. Specifically, when the biological information measuring device 1 is in the measurement mode, if an operation signal representing that the third button 153 is pressed through the long pressing is output from the third button 153, the MCU 136 performs a process of resetting the measurement state by the reset circuit 141.

The measurement state reset by the reset circuit 141 is a measurement state where the lap pace information and the cumulative movement distance information are initialized, and is also a measurement state where the user does not move at all after the operation mode is changed to the measurement mode. Such a measurement state is referred to as a measurement initial state.

In the biological information measuring device 1 according to the present exemplary embodiment, the fourth button 154 does not have a function regarding the switching between the operation modes. The fourth button 154 has a function of setting turning on or off the light 137. Specifically, when an operation signal representing that the fourth button 154 is pressed through the short pressing is output from the fourth button 154, the MCU 136 performs a process of allowing the light 137 to emit light only for a predetermined period of time and irradiating the display section 120 with light.

The operation buttons 151 to 154 are used to switch between the operation modes (the measurement mode and the time display mode) or to perform a display setting or various setting inputs on the display section 120.

The description will be made by referring back to FIG. 4.

The vibration section 129 is a device for notifying the user of an alarm through vibrating, and includes, for example, a rotational weight having eccentricity. When a current flows in the vibration section 129, vibration occurs by which the rotational weight rotates, and thus, it is possible to perform a notification by transferring the vibration to the arm of the user through the biological information measuring device 1.

The accelerometer 138 is a sensor that is provided on the circuit board 40 to detect accelerations in three axis directions. That is, as the three axis directions, when the user wears the biological information measuring device 1 on the arm and runs with their thumb up, a running direction of the user is an X-axis direction, a vertical motion direction (a gravity direction) of the user is a Y-axis direction, and a horizontal motion direction of the user is a Z-axis direction.

The pulse sensor 160 includes the photoelectric sensor that measures a pulse as the biological information as mentioned above, obtains a pulse signal of the user, and outputs the obtained signal to the MCU 136.

Figure 8:
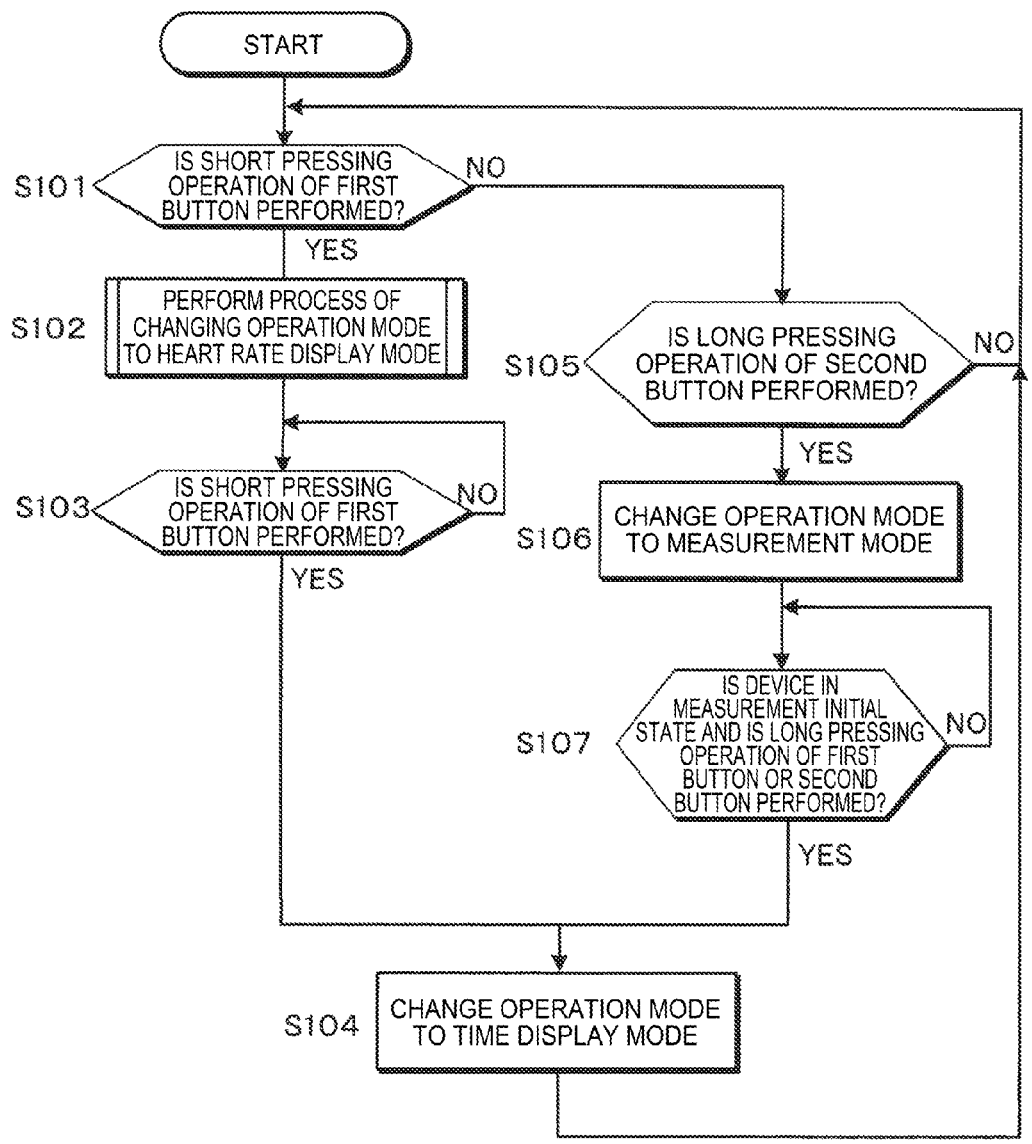
FIG. 8 is a diagram showing a flowchart of a process related to switching between operation modes.

FIG. 8 is a diagram showing a flowchart of a process of switching between the operation modes. The biological information measuring device 1 according to the present exemplary embodiment is normally set in the time display mode shown in FIG. 5 as stated above, and changes the operation mode to another mode in response to the operation of the operation buttons 151 to 154. Hereinafter, an example of the process of switching between the operation modes will be described in detail with reference to FIG. 8.

While the biological information measuring device 1 is set in the time display mode, the MCU 136 determines whether or not the operation signal is input in response to the short pressing operation of the first button 151 (step S101). When the determined result of step S101 is positive, in other words, when the operation signal in response to the short pressing operation of the first button 151 is input, the MCU 136 performs a "process of changing the operation mode of the biological information measuring device 1 to the heart rate display mode" (step S102).

Figure 9:
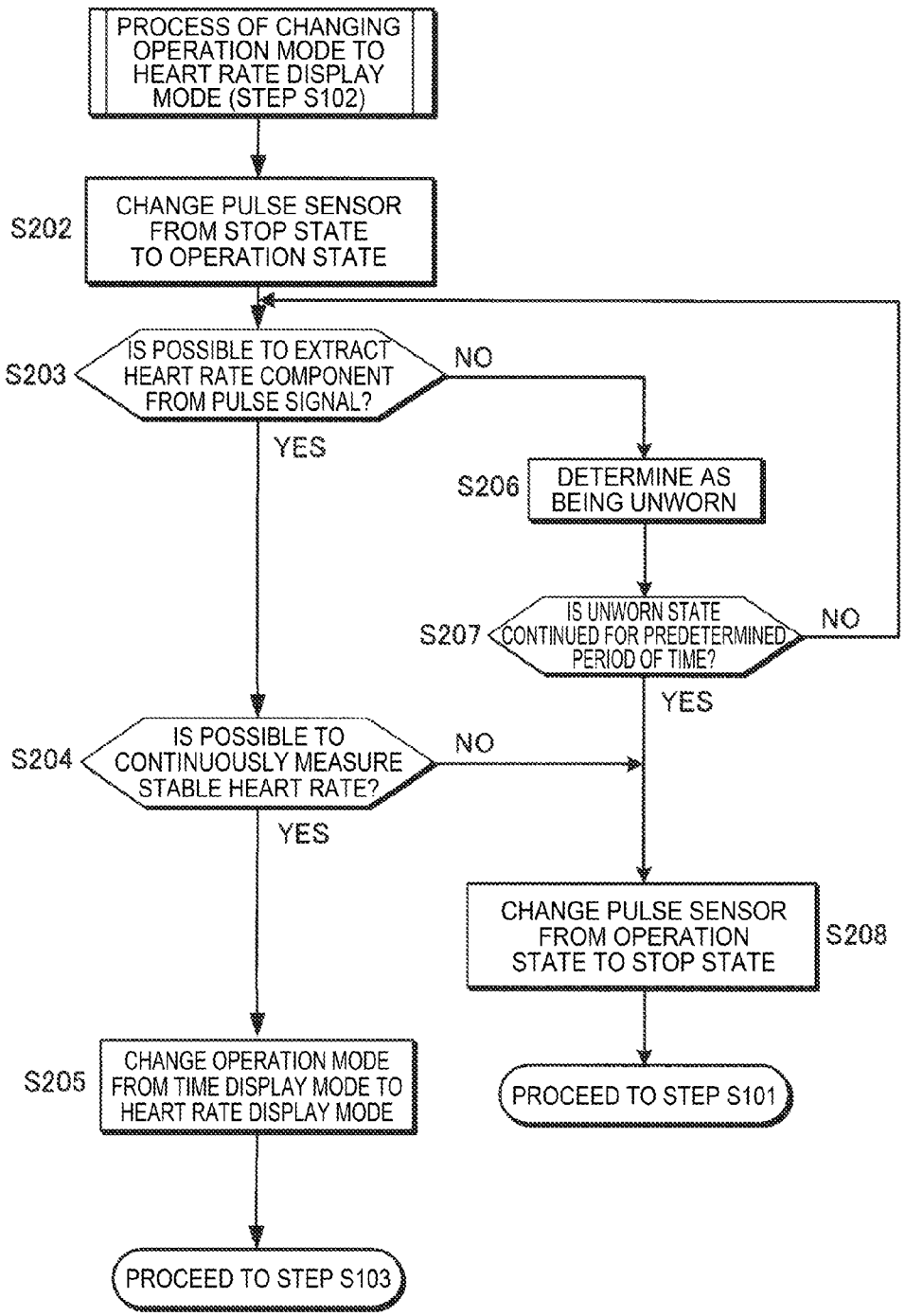
FIG. 9 is a diagram showing a flowchart (subroutine of step S102) of a process of changing the operation mode to the heart rate display mode.

FIG. 9 is a diagram showing a subroutine (a flowchart of a process of changing the operation mode to the heart rate display mode) of step S102.

The process shown in FIG. 9 is a process in consideration with the following problems. That is, while the biological information measuring device 1 is not worn on the user, when the first button 151 is pressed through the short pressing due to any cause, the pulse sensor 160 is set in the operation state even though the pulse signal of the user is not obtained, and power consumption and process load may be wastefully increased. Such a phenomenon may have a bad influence on an effect of reducing power consumption and process load achieved by the heart rate display mode which is a characterizing portion of the biological information measuring device 1 according to the present exemplary embodiment.

Thus, the biological information measuring device 1 according to the present exemplary embodiment determines whether or not the biological information measuring device 1 is worn on the user by performing the process of the flowchart shown in FIG. 9, and maintains the operation mode in the time display mode without changing the operation mode to the heart rate display mode when the device is not worn on the user.

The process of the flowchart shown in FIG. 9 is a process performed by the MCU 136 for the preparation period of time described with reference to FIG. 7B.

The MCU 136 sets the pulse sensor 160 in the operation state (step S202). Thereafter, the MCU 136 determines whether or not a heart rate component can be extracted from the pulse signal output from the pulse sensor 160 (step S203). When the determined result in step S203 is negative, in other words, when it is difficult to extract the heart rate component, the MCU 136 determines that the biological information measuring device 1 is not worn on the user (is unworn) (step S206). Here, the MCU 136 determines whether or not an unworn state is continued for a predetermined period of time (step S207). When the determined result in step S207 is negative, in other words, when the unworn state is not continued for the predetermined period of time, the MCU 136 returns to the process of step S203. Meanwhile, when the determined result of step S207 is positive, in other words, when the unworn state is continued for the predetermined period of time, the MCU 136 sets the pulse sensor 160 in the stop state (step S208), performs transition to the display screen of the time display mode without changing the operation mode to the heart display mode, and returns to the process of step S101.

Incidentally, when the determined result of step S203 is positive, in other words, when the heart rate component can be extracted, the MCU determines whether or not the heart rate is continuously stable and is measured (the pulse signal is not rapidly unstable) (step S204). When the determined result of step S204 is negative, in other words, when the heart rate is continuously stable and is not measured (the pulse signal is rapidly unstable), the MCU proceeds to the process of step S208. Meanwhile, when the determined result of step S204 is positive, in other words, when the heart rate is continuously stable and is measured (the pulse signal is not rapidly unstable), the MCU sets the biological information measuring device 1 in the heart rate display mode (step S205), and the MCU proceeds to the process of step S103, to be described below.

After the process of step S205 is completed, in other words, after the operation mode of the biological information measuring device 1 is changed to the heart rate display mode, the MCU 136 re-determines whether or not the operation signal in response to the short pressing operation of the first button 151 is input (step S103). When the determined result of step S103 is positive, in other words, when the operation signal in response to the short pressing operation of the first button 151 is input, the MCU 136 performs a process of changing the operation mode of the biological information measuring device 1 to the time display mode (step S104), and returns to the process of step S101.

Meanwhile, when the determined result of step S103 is negative, in other words, when the operation signal in response to the short pressing operation of the first button 151 is not input, the MCU 136 returns to the process of step S103. That is, the biological information measuring device 1 maintains the heart rate display mode.

Incidentally, when the determined result of step S101 is negative, in other words, when the operation signal in response to the short pressing operation of the first button 151 is not input, the MCU 136 determines whether or not the operation signal in response to the long pressing operation of the second button 152 is input (step S105). When the determined result of step S105 is negative, in other words, when the operation signal in response to the long pressing operation of the second button 152 is not input, the MCU returns to the process of step S101.

Meanwhile, when the determined result of step S105 is positive, in other words, when the operation signal in response to the long pressing operation of the second button 152 is input, the MCU 136 performs a process of changing the operation mode of the biological information measuring device 1 to the measurement mode (step S106).

After the process of step S106 is completed and the operation mode of the biological information measuring device 1 is changed to the measurement mode, the MCU 136 determines whether or not the biological information measuring device 1 is in the "measurement initial state" and the operation signal in response to the long pressing operation of the first button 151 or the second button 152 is input (step S107). When the determined result of step S107 is positive, in other words, when the operation signal in response to the short pressing operation of the first button 151 is input, the MCU 136 performs a process of changing the operation mode of the biological information measuring device 1 to the time display mode (step S104), and returns to step S101.

Meanwhile, when the determined result of step S107 is negative, in other words, when the biological information measuring device 1 is not in the measurement initial state and the operation signal in response to the long pressing operation of the first button 151 or the second button 152 is not input even in the measurement initial state, the MCU returns to the process of step S107. That is, the biological information measuring device 1 maintains the measurement mode.

After the process of step S104 is completed and the operation mode of the biological information measuring device 1 is changed to the time display mode, the MCU returns to the process of step S101.

The "zone" may be specifically set as follows by the user.

Figure 10:
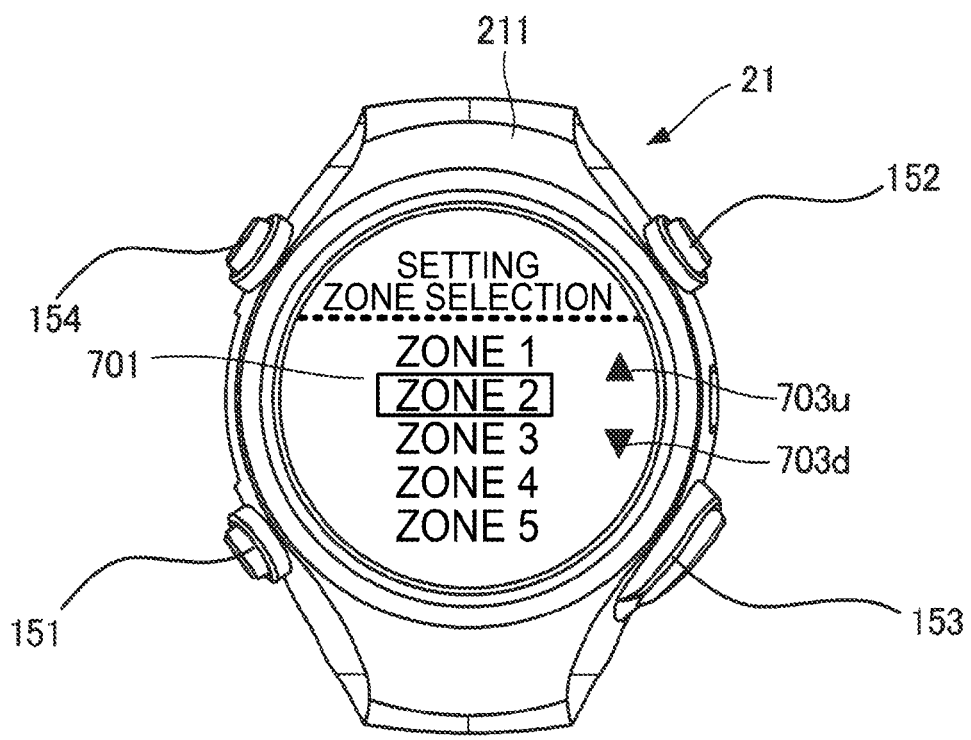
FIG. 10 is a diagram showing an example of a screen displayed on the display section when a user sets zones.
Figure 11:
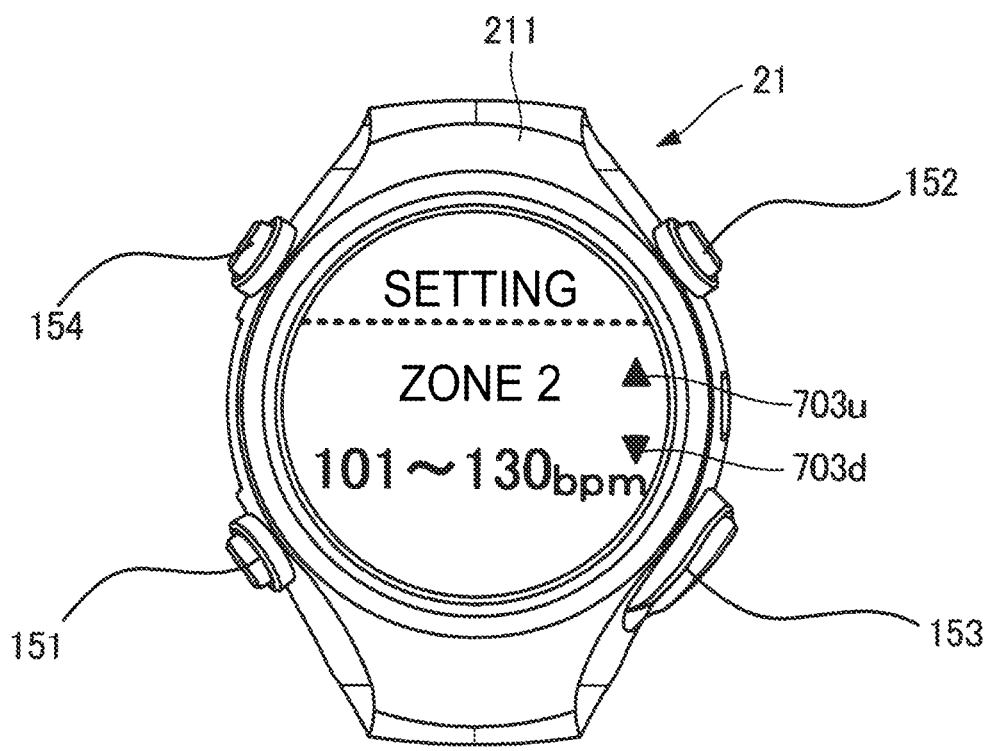
FIG. 11 is a diagram showing an example of a screen displayed on the display section when the user sets the zones.

FIGS. 10 and 11 are diagrams showing an example of the screen displayed on the display section 120 when the user sets the zone.

When a predetermined operation is performed using the operation buttons 151 to 154 when the biological information measuring device 1 is in the time display mode, a "setting zone selecting screen" shown in FIG. 10 is displayed on the display section 120. The user selects a zone desired to set a value range on the setting zone selecting screen by moving a selection mark 701 up and down and determines the selected zone. An up mark 703*u* representing an up movement of the selection mark 701 corresponds to the second button 152, and a down mark 703*d* representing a down movement of the selection mark 701 corresponds to the third button 153. For example, the first button 151 is used to determine the zone to which the selection mark 701 is applied, as a setting target.

For example, on the setting zone selecting screen shown in FIG. 10, when Zone 2 is selected and is determined as the setting target, a value range setting screen shown in FIG. 11 is displayed on the display section 120. The user sets a value range of the zone (Zone 2 in this example) in response to a predetermined operation using the operation buttons 151 to 154.

FIGS. 12A and 12B are diagrams showing a setting example of the value range of the zone.

The setting example (normal setting example) shown in FIG. 12A is an example which is exclusively set such that the value ranges of the respective zones do not overlap with each other. That is, in the example shown in the drawing, Zone 1 is set in a value range of 30 to 100 bpm, Zone 2 is set in a value range of 101 to 130 bpm, Zone 3 is set in a value zone of 131 to 160 bpm, Zone 4 is set in a value zone of 161 to 190 bpm, and Zone 5 is set in a value zone of 191 to 240 bpm.

The setting example (overlap setting example) shown in FIG. 12B is an example which is set such that the value ranges of at least two or more zones (two zones in this example) overlap. That is, in the example shown in the drawing, Zone 1 is set in a value range of 30 to 100 bpm, Zone 2 is set in a value range of 101 to 130 bpm, Zone 3 is set in a value range of 131 to 165 bpm, Zone 4 is set in a value range of 160 to 190 bpm, and Zone 5 is set in a value range of 191 to 240 bpm. In the drawing, the shaded zones are zones set such that the value ranges overlap with each other.

Here, the zone display corresponding to the normal setting example shown in FIG. 12A is the zone display 506 shown in FIG. 6. That is, when the heart rate at the relevant point in time is 165 bpm in the measurement mode, a circle display that represents Zone 4 to which the heart rate of 165 belongs and that is counted as number four from the left is turned on (the black display in this drawing). The user can easily grasp that their heart rate belongs to which zone of the zones set to be a desired value range by viewing the zone display 506.

Figure 13:
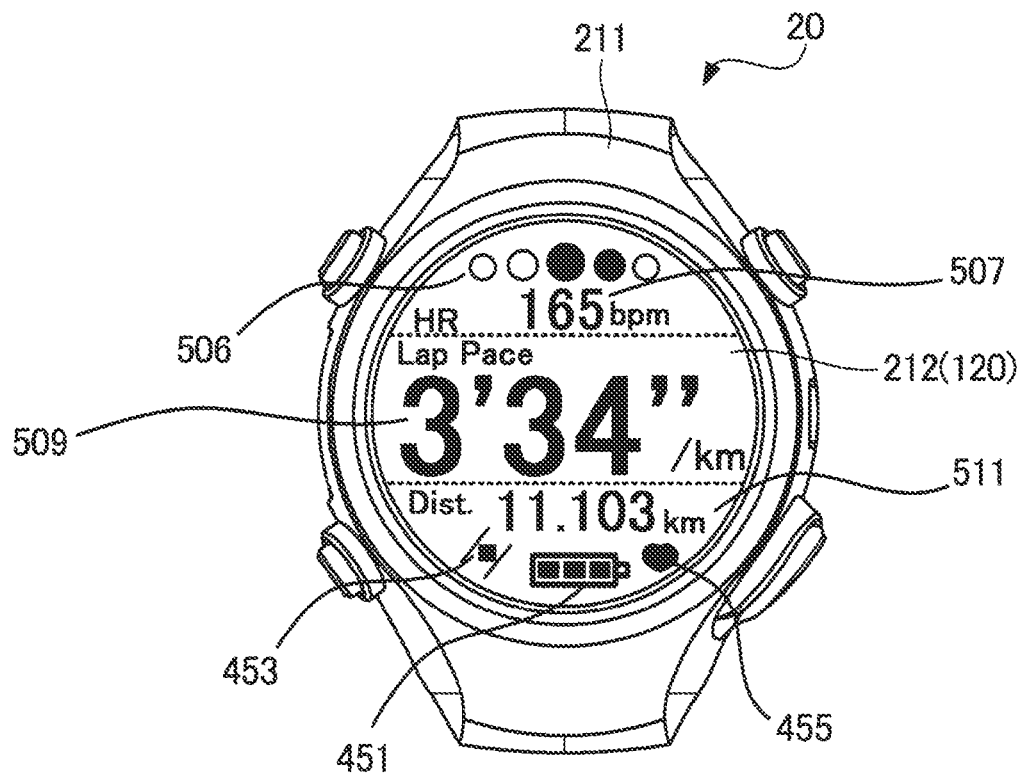
FIG. 13 is a diagram showing a display example of the display section in the measurement mode when the value ranges of the zones overlap.

Meanwhile, the zone display corresponding to the overlap setting example shown in FIG. 12B is a zone display 506 shown in FIG. 13. That is, FIG. 13 is a diagram showing a display example of the display section 120 in the measurement mode when the value ranges of the zones are set so as to overlap with each other. As shown in this drawing, when the heart rate at the relevant point in time is 165 bpm in the measurement mode, the heart rate of 165 belongs to Zone 3 and Zone 4. Accordingly, a circle display which represents Zone 3 and is counted as number three from the left and a circle display which represents Zone 4 and is counted as number four from the left are turned on (the black display in this drawing). The user can easily grasp that their heart rate belongs to which zone of the zones set to be a desired value range by viewing the zone display 506.

For example, by setting the value ranges of the zones to overlap with each other in this manner, it is easy to conduct a flexible running plan in which a heart rate corresponding to the upper half of the value range related to the zone where the heart rate is lower than the highest heart rate by one level is allowed in other sections while achieving the zone where the heart rate is the highest in a specific section of a running path.

In the configuration of the biological information measuring device according to the related art, it is difficult to set the zones in this manner. In addition, in the configuration of the biological information measuring device according to the related art, since it is difficult to individually express the plurality of zones as shown in the zone display 506, the device can cope with only the zones to which the value ranges are exclusively set.

Figure 14:
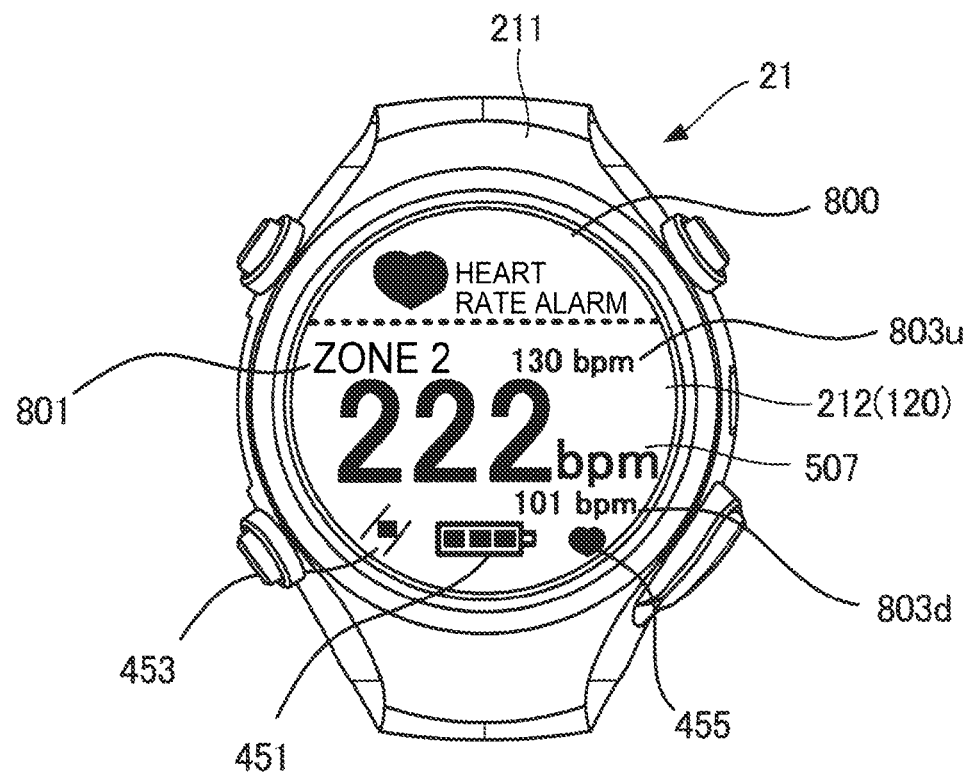
FIG. 14 is a diagram showing a display example of the display section when a heart rate alarm is operated.

FIG. 14 is a diagram showing a display example of the display section 120 when a "heart rate alarm" for giving an alarm to the user is operated. The "heart rate alarm" has a function of displaying an alarm screen shown in FIG. 14 on the display section 120 by the MCU 136 when the heart rate of the user belongs to an "alarm zone" which is one zone or a plurality of zones which is an alarming target. When the heart rate alarm is operated, the display section 120 functions as an alarm section for giving an alarm to the user. Here, the "alarm zone" may be set through a predetermined operation of the user using the operation buttons 151 to 154.

When the heart rate alarm is operated, the user may be alerted by outputting a predetermined alarm sound through a speaker (not shown), or the user may be alerted by transmitting vibration to the arm of the user by the vibration section 129.

In the example of the alarm screen shown in FIG. 14, an alarm indicator 800 indicating that the heart rate alarm is operated, the heart rate information 507 at the relevant point in time, an alarm zone indicator 801 indicating the alarm zone, and a lower limit 803d and an upper limit 803u of the alarm zone are displayed on the display section 120.

Although it has been described in the aforementioned example that the heart rate alarm is operated when the heart rate of the user belongs to the alarm zone, the heart rate alarm may be operated when the heart rate of the user is out of a predetermined zone (target zone). In this case, the user sets one zone or a plurality of target zones which is excluded from the alarming target, and the MCU 136 controls the alarm section (the display section 120 or the vibration section 129) to output an alarm when the heart rate does not belong to the target zones. The heart rate alarm that sets the alarm zone and the heart rate alarm that sets the target zone are substantially equivalent.

As described above, according to the exemplary embodiment of the disclosure, it is possible to provide the biological information measuring device capable of setting the value ranges of the heart rate corresponding to the respective zones such that the plurality of zones overlap each other and appropriately presenting the zones set in this manner to the user.

Although the present exemplary embodiment has been described in detail as stated above, it should be understood to those skilled in the art that various modifications are possible without substantially departing from the new matter and effect of the disclosure. Accordingly, such modification examples are included in the scope of the disclosure. For example, in the present specification and drawings, the terms described together with other terms having the wider meaning or the same meaning at least once may be replaced with the other terms in any one of the specification or the drawing. The configuration and operation of the biological information measuring device are not limited to the description of the present exemplary embodiment, and may be variously modified.

First Modification Example

In the biological information measuring device 1 according to the exemplary embodiment, the process content of step S103 of the flowchart shown in FIG. 8 may be changed as follows.

That is, a condition in which the MCU proceeds to the processes from step S103 to step S104 and performs transition to the time display mode may be set as "for example, a predetermined period of time such as 1 minute elapses" in place of the "short pressing operation of the first button 151".

In this case, the MCU 136 determines whether or not a predetermined period of time elapses in step S103. When the determined result is positive, the MCU proceeds to the process of step S104. The MCU may proceed to the process of step S104 after the predetermined period of time elapses, and may proceed to the process of step S104 through the short pressing operation of the first button 151 before the predetermined period of time elapses.

Second Modification Example

In the biological information measuring device 1 according to the exemplary embodiment, the process content of step S107 of the flowchart shown in FIG. 8 may be changed as follows.

That is, a condition in which the MCU proceeds to the processes from step S107 to step S104 and performs transition to the time display mode may be set as "for example, a predetermined period of time such as 1 hour elapses" in place of the "long pressing operation of the first button 151 or the second button 152 in the measurement initial state".

In this case, the MCU 136 determines whether or not a predetermined period of time elapses in step S107. When the determined result is positive, the MCU proceeds to the process of step S104. The MCU may proceed to the process of step S104 after the predetermined period of time elapses, and may proceed to the process of step S104 through the long pressing operation of the first button 151 or the second button 152 in the measurement initial state before the predetermined period of time elapses.

Application Example

In addition to the respective modes, a fourth mode in which the antenna 130 and the pulse sensor 160 can be individually set in the operation state and the stop state may be added.

A drive time is changed depending on an operation status. For example, when the measurement of a position by GPS (the antenna 130) every second and the measurement of the pulse information by the pulse sensor 160 are simultaneously performed, the biological information measuring device 1 may be driven for 20 hours. When the measurement of the position by the GPS every second is performed while the pulse sensor 160 is in the stop state and the antenna 130 is in the operation state, the biological information measuring device 1 may be driven for 24 hours. When the measurement of the pulse sensor 160 is performed while the antenna 130 is in the stop state, the biological information measuring device 1 may be driven for 60 hours.

What is claimed is:

1. A biological information measuring device comprising:
   a display; and
   a processor adapted
      to generate heart rate information representing a heart rate of a living body,
      to specify a heart rate range of a plurality of predetermined heart rate ranges to which the heart rate belongs based on the heart rate information, and
      to control the display to display that the heart rate belongs to the specified heart rate range;
   wherein the plurality of heart rate ranges include a first heart rate range from a first lower limit of heart rate to a first upper limit of heart rate, and a second heart rate range from a second lower limit of heart rate which is greater than the first lower limit and less than the first upper limit to a second upper limit of heart rate, and
   wherein the processor is further adapted to specify that the heart rate belongs to the first heart rate range and the second heart rate range when the heart rate is greater than the second lower limit and is less than the first upper limit, and to control the display to simultaneously display that the heart rate belongs to the first heart rate range and the second heart rate range.

2. The biological information measuring device according to claim 1,
   wherein the display includes a first display region and a second display region, and
   wherein the processor is further adapted
      to control the first display region to display that the heart rate belongs to the first heart rate range, and
      to control the second display region to display that the heart rate belongs to the second heart rate range.

3. The biological information measuring device according to claim 1, further comprising:
   an alarm; and
   wherein the processor is further adapted
      to set an alarm heart rate range that includes at least one heart rate range, and
      to control the alarm to give an alarm when the heart rate belongs to the alarm heart rate range.

4. The biological information measuring device according to claim 1, further comprising:
   an alarm; and
   wherein the processor is further adapted
      to set a target heart rate range that includes at least one heart rate range, and
      to control the alarm to give an alarm when the heart rate does not belong to the target heart rate range.

5. The biological information measuring device according to claim 3,
   wherein the display includes a first display region and a second display region allocated to the display, and
   the processor is further adapted
      to control the display to display an alarm in a region to which the first display region and the second display region are allocated when the heart rate belongs to the alarm heart rate range.

6. The biological information measuring device according to claim 1, wherein the processor is further adapted to set at least one of the first lower limit, the first upper limit, the second lower limit, and the second upper limit based on an input of a user.

7. The biological information measuring device according to claim 3, wherein the processor is adapted to set the alarm heart rate range based on an input of a user.

8. The biological information measuring device according to claim 4, wherein the processor is adapted to set the target heart rate range based on an input of a user.

* * * * *